United States Patent
Petrus Van Dun et al.

(10) Patent No.: US 8,859,863 B2
(45) Date of Patent: *Oct. 14, 2014

(54) FERTILISATION INDEPENDENT FRUIT FORMATION IN TOMATO

(75) Inventors: Cornelis Maria Petrus Van Dun, Roosendaal (NL); Pieter Martijn Eggink, Oostvoorne (NL); Dörthe Bettina Dräger, Den Hoorn (NL)

(73) Assignee: Rijk Zwaan Zaadteelt en Zaadhandel B.V., De Lier (NL)

( * ) Notice: Subject to any disclaimer, the term of this patent is extended or adjusted under 35 U.S.C. 154(b) by 0 days.

This patent is subject to a terminal disclaimer.

(21) Appl. No.: 13/310,077

(22) Filed: Dec. 2, 2011

(65) Prior Publication Data

US 2012/0164303 A1    Jun. 28, 2012

Related U.S. Application Data

(63) Continuation-in-part of application No. PCT/EP2010/058741, filed on Jun. 21, 2010.

(30) Foreign Application Priority Data

Jun. 22, 2009   (EP) .................................... 09163385

(51) Int. Cl.
- *A01H 5/00*  (2006.01)
- *C12N 5/04*  (2006.01)
- *A23K 1/00*  (2006.01)
- *A01H 5/08*  (2006.01)

(52) U.S. Cl.
CPC ........................................ *A01H 5/08* (2013.01)
USPC ................. 800/317.4; 435/411; 426/615

(58) Field of Classification Search
USPC ....................................................... 800/317.4
See application file for complete search history.

(56) References Cited

U.S. PATENT DOCUMENTS

| | | | |
|---|---|---|---|
| 2009/0089900 A1* | 4/2009 | Roque Mesa et al. | 800/290 |
| 2010/0146656 A1* | 6/2010 | De Haan et al. | 800/260 |

FOREIGN PATENT DOCUMENTS

| | | |
|---|---|---|
| EP | 1428425 | 6/2004 |
| WO | WO 2009/005343 | 1/2009 |

OTHER PUBLICATIONS

Hodgkin, Seven types of pleiotropy, 42 Int. J. Dev. Biol., 501-505 at 501 (1998).*

(Continued)

*Primary Examiner* — Ashwin Mehta
*Assistant Examiner* — Rebecca Coobs
(74) *Attorney, Agent, or Firm* — Vedder Price P.C.; Thomas J. Kowalski; Deborah L. Lu

(57) ABSTRACT

The invention relates to tomato plants which may comprise the trait fertilization independent fruit formation, which may be obtainable by introgression from a plant, representative seed of which was deposited with the NCIMB under accession number NCIMB 41626, NCIMB 41627, NCIMB 41628, NCIMB 41629, NCIMB 41630 or NCIMB 41631. Such tomato plant may be obtainable by crossing plants, representative seed of which was deposited with the NCIMB under accession number NCIMB 41626, NCIMB 41627, NCIMB 41628, NCIMB 41629, NCIMB 41630 or NCIMB 41631, with a plant not showing the trait to obtain an F1 population; selfing plants from the F1 population to obtain an F2 population; preventing pollination of the F2 plants and allowing fruit formation to occur; and selecting plants producing fruits as plants showing fertilization independent fruit formation. The invention further relates to parthenocarpic fruits, seeds of the plants and propagation material of the plant.

19 Claims, 11 Drawing Sheets
(11 of 11 Drawing Sheet(s) Filed in Color)

(56) References Cited

OTHER PUBLICATIONS

Kim et al., EMS Mutagenesis of Arabidopsis, in Methods in Molecular Biology: *Arabidopsis* Protocols 323 (2d ed. 2006).*

Mazzucato et al. (Characterization of genes controlling stamen identity and development in a parthenocarpic tomato mutant indicates a role for the DEFICIENS ortholog in the control of fruit set, 132 Physiologia Plantarum, 526-537 (2008)).*

Schauer et al., Metabolic profiling of leaves and fruit of wild species tomato: a survey of the *Solanum lycopersicum* complex, 56 J. Exp. Botany No. 410, 297-307 (2005)).*

D. Beraldi, et al., Fine Mapping of the Parthenocarpic Fruit (pat) Mutation in Tomato, Theoretical Applied Genetics (2004) vol. 108, p. 209-219.

Marc Goetz, et al., Expression of Aberrant Forms of Auxin Response Factor8 Stimulates Parthenocarpy in *Arabidopsis* and Tomato, Plant Physiology (2007) vol. 145, p. 351-366.

Benoit Gorguet, et al., Mapping and Characterization of Novel Parthenocarpy QTLs in Tomato, Theoretical Applied Genetics (2008) vol. 116, p. 755-767.

* cited by examiner

Fig. 1

Fig. 2A-1
Fig. 2B-1
|  | emas. | not emas. |
|---|---|---|
| area (mm²) | 800.74 | 2418.90 |
| st. dev. | 100.76 | 42.55 |
Fig. 2C
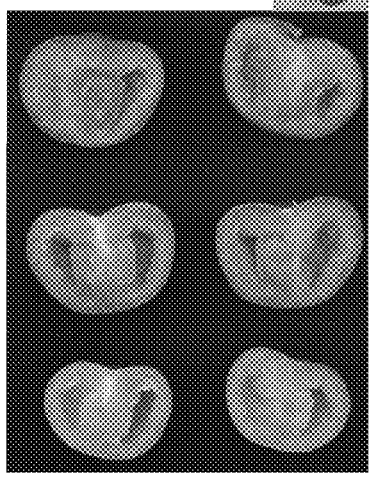
Fig. 2A-2
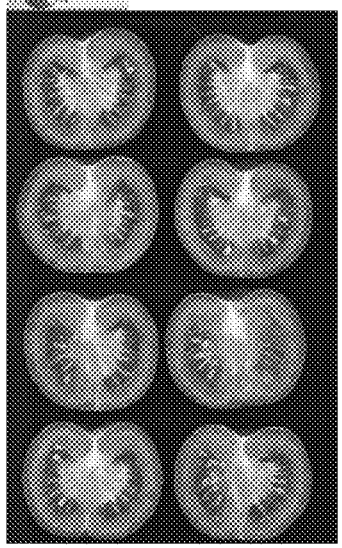
Fig. 2B-2
Fig. 2

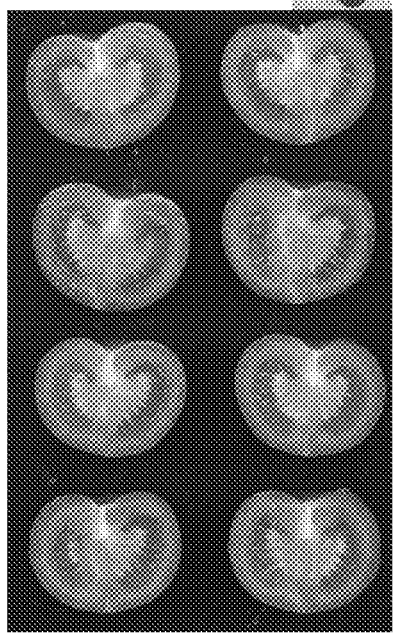
Fig. 3A-1
Fig. 3A-2
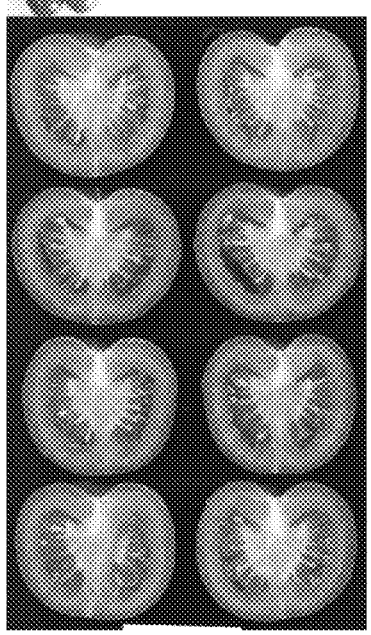
Fig. 3B-1
Fig. 3B-2
|  | emas. | not emas. |
|---|---|---|
| area (mm²) | 1789.64 | 2778.92 |
| st. dev. | 62.45 | 85.24 |
Fig. 3C
Fig. 3

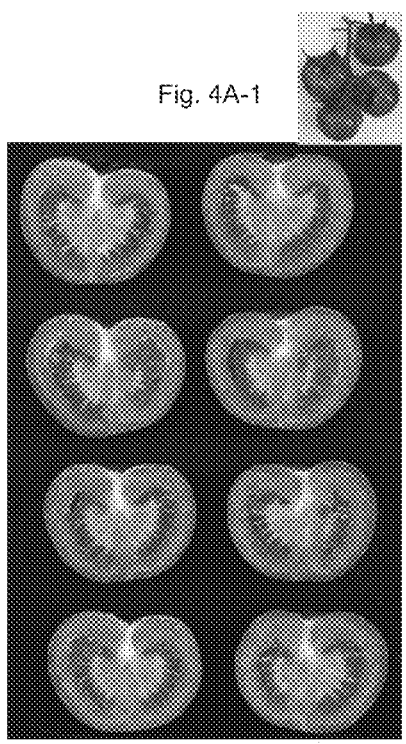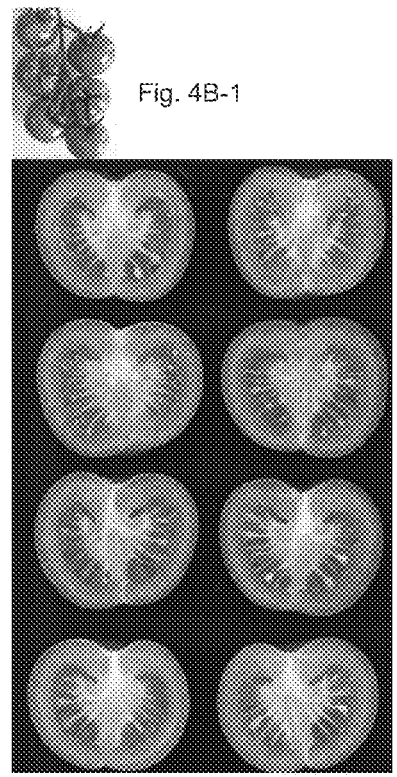
Fig. 4A-1
Fig. 4B-1
Fig. 4C
Fig. 4
Fig. 4A-2
Fig. 4B-2

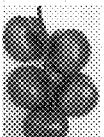
Fig. 5A-1
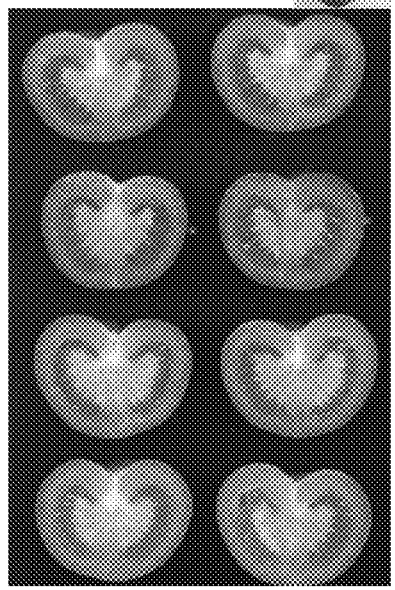
Fig. 5A-2
| | emas. | not emas. |
|---|---|---|
| area (mm²) | 1918.29 | 2661.30 |
| st. dev. | 69.92 | 130.14 |
Fig. 5C
Fig. 5B-1
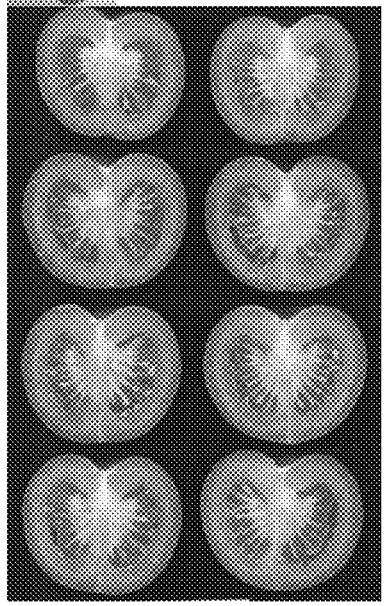
Fig. 5B-2
Fig. 5

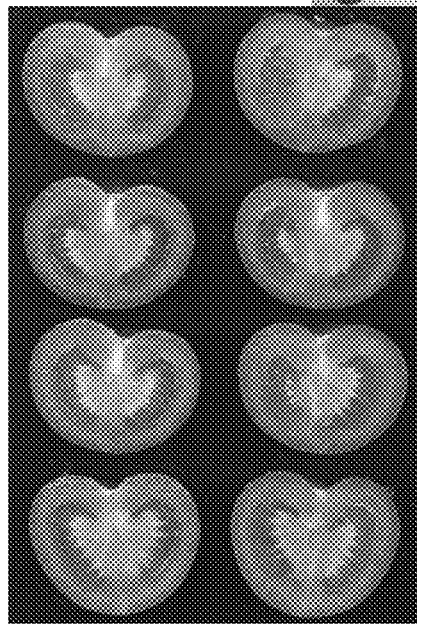
Fig. 6A-1
Fig. 6A-2
Fig. 6C
Fig. 6
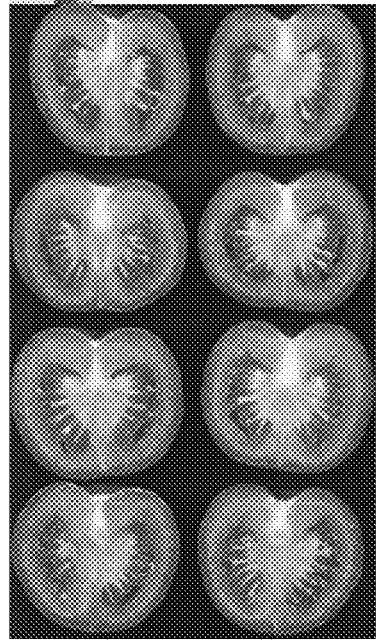
Fig 6B-1
Fig. 6B-2

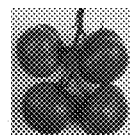
Fig. 7A-1
Fig. 7B-1
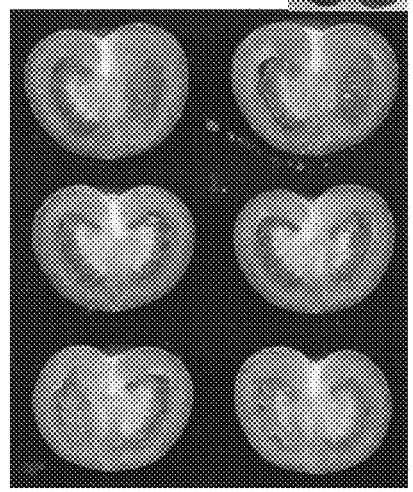
Fig. 7A-2
Fig. 7C
Fig. 7
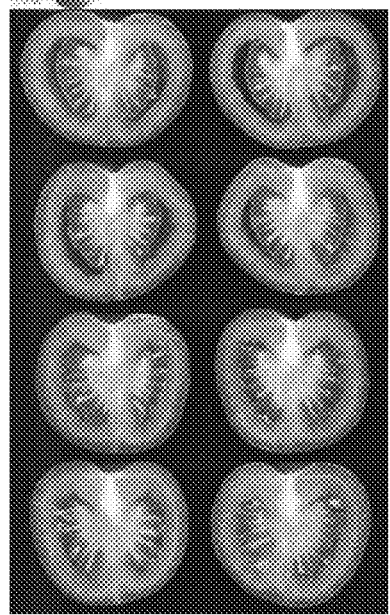
Fig. 7B-2

Fig. 8A-1
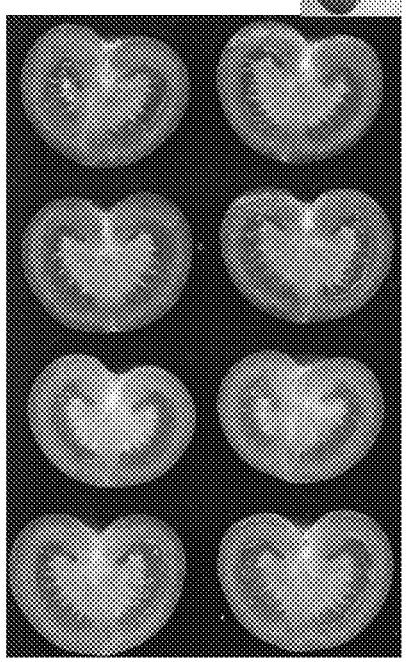
Fig. 8A-1
|  | amas. | not amas. |
|---|---|---|
| area (mm²) | 2446.15 | 2846.86 |
| st. dev. | 133.25 | 169.40 |
Fig. 8C
Fig. 8B-1
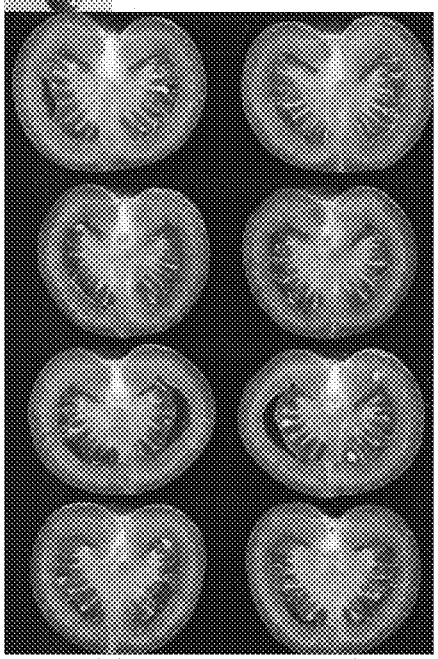
Fig. 8A-2
Fig. 8

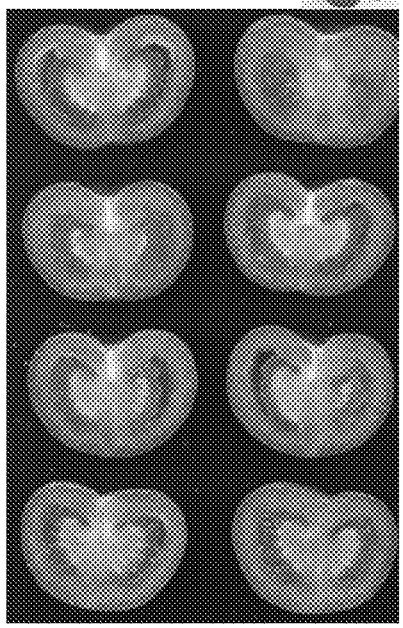
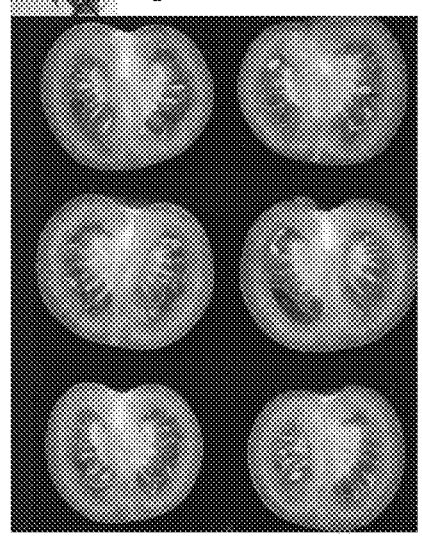
Fig. 9A-1
Fig. 9A-2
Fig. 9B-1
Fig. 9B-2
Fig. 9C
Fig. 9

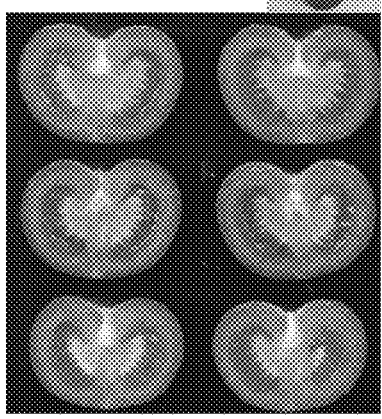
Fig. 10A-1
Fig. 10A-2
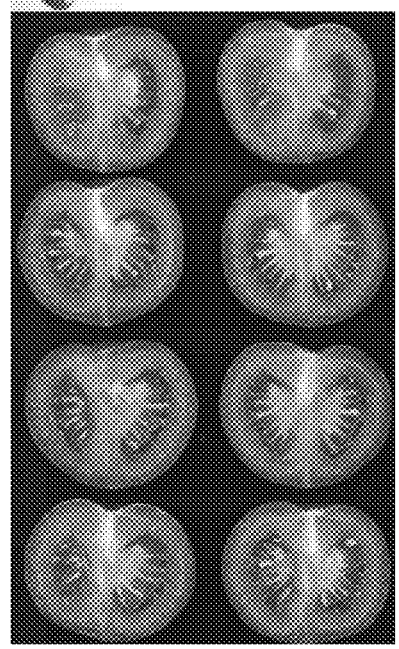
Fig. 10B-1
Fig. 10B-2
|  | emas. | not emas. |
|---|---|---|
| area (mm²) | 2274.18 | 2488.62 |
| st. dev. | 135.06 | 76.31 |
Fig. 10C
Fig. 10

Fig. 11A-1
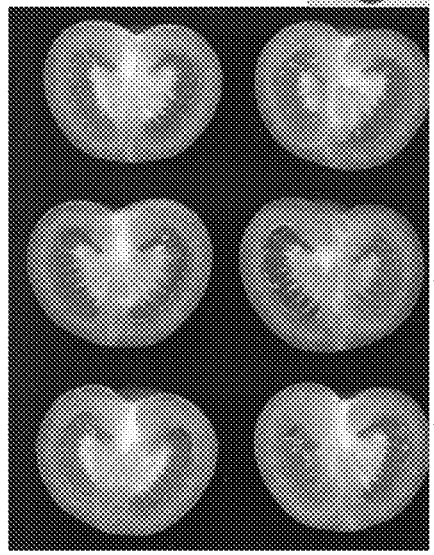
Fig. 11A-2
|  | emas. | not emas. |
|---|---|---|
| area (mm²) | 2214.88 | 2670.36 |
| st. dev. | 100.80 | 38.63 |
Fig. 11C
Fig. 11B-1
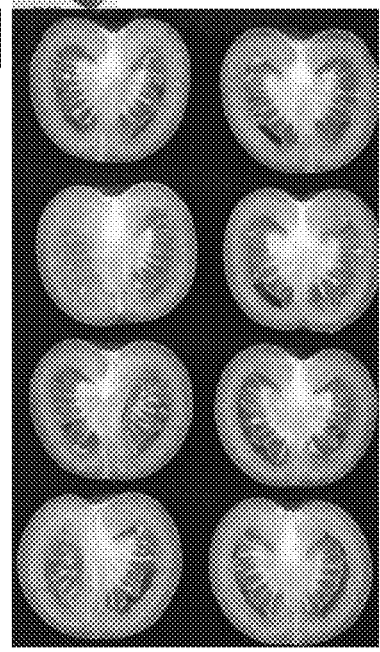
Fig. 11B-2
Fig. 11

FERTILISATION INDEPENDENT FRUIT FORMATION IN TOMATO

RELATED APPLICATIONS AND INCORPORATION BY REFERENCE

This application is a continuation-in-part application of international patent application Serial No. PCT/EP2010/058741 filed 21 Jun. 2010, which published as PCT Publication No. WO 2010/149628 on 29 Dec. 2010, which claims benefit of European patent application Serial No. 09163385.9 filed 22 Jun. 2009.

The foregoing applications, and all documents cited therein or during their prosecution ("appin cited documents") and all documents cited or referenced in the appin cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The invention relates to plants and plant parts, in particular fruity vegetables, which may be altered with respect to their mode of fruit formation. More in particular, this invention relates to tomato (*Solanum lycopersicum* L.) plants that may show fruit formation independent of fertilisation. This mode of fruit formation is often referred to as parthenocarpy. The invention also relates to seeds that may be able to grow into plants that show fertilization independent fruit formation.

The invention further relates to methods for obtaining said plants with altered genotypes and seeds thereof, which may show an altered mode of fruit formation which is independent of fertilisation.

BACKGROUND OF THE INVENTION

Breeding of fruity vegetables like tomato aims at the production of commercial varieties optimally adapted to a professional production environment in order to produce marketable products. Many characteristics need to be taken into account during selection which relate to both input and output traits. One of the very important traits in this respect relates to fruit set, in particular to fruit set under unfavourable environmental conditions such as high or low temperatures and drought. Such conditions can be detrimental for normal pollination and thereby fertilisation which leads to poor fruit set and as a consequence yield loss. When fertilisation independent fruit formation or parthenocarpy can be harnessed as a trait, it is an important characteristic that can significantly contribute to an economically more efficient production of tomato fruits.

In addition to contributing to harvest security, parthenocarpy is also important for fruit quality. Parthenocarpic tomato fruits have been mentioned to have a better flavour as well as a higher dry matter content as compared to seeded fruits. The higher level of soluble solids is especially important for processing tomatoes which are used in industry for paste production. In addition, such fruit can be advantageous for the fresh cut industry which requires firm fruits which are not leaky. Furthermore, industrial or domestic applications which require seed removal from the fruits can benefit strongly from parthenocarpy.

Fruit set normally depends on fertilisation. Fertilisation is the process in which both the egg cell and central cell contained within the ovule are fused with a sperm cell delivered by the pollen tube. This so-called double fertilisation is the step which triggers a cascade of events leading to the formation of the embryo and endosperm and finally to a mature seed. The developing seeds and surrounding tissues generate a signal which stimulates the outgrowth of the ovary and its development into a fleshy fruit.

Apparently, fertilisation lifts a certain developmental barrier which prevents fruit formation. This mechanism assures the fruit formation to be dependent on the formation of seeds which makes sense given the biological role of fruits in seed dispersal. The knowledge of the physiological and molecular events which play a role in the initial steps of fruit formation, however, is fragmentary. The involvement of the plant hormones auxin and gibberellin has been extensively documented although their precise role remains elusive. The application of either auxin or gibberellin to the unfertilised ovule leads in many plant species including tomato to fruit formation. In fact, these hormones are applied in practice to improve fruit set when greenhouse conditions are suboptimal. Although the application of auxin and gibberellin has some practical value it increases costs and it may lead to irregularities in fruit shape. In addition to these exogenous effects, it is assumed that the hormones auxin and gibberellin also play a role during fertilisation dependent fruit formation although it is not clear which tissues are the actual source of these hormones. In addition, the hierarchy of these hormones as well as the downstream regulatory network is still largely unknown. Other hormones, such as cytokinins, abscisic acid, ethylene and brassinosteroid also seem to play a role in fruit formation.

It seems likely that many genes are involved in fertilisation dependent fruit formation. However, currently only a few genes have been characterised in this respect. For example, the DGT (diageotropica), the ARF7 and IAA9 genes of tomato have been characterised in detail as well as the AUCSIA genes. In *Arabidopsis* the fwf mutant has been described which contains a mutation in the ARF8 gene which leads to the formation of parthenocarpic siliques. It has been proposed that auxin which is formed upon fertilisation lifts the inhibitory ARF8 activity which results in a response leading to fruit formation. A genetic lesion in the ARF8 gene may simulate the auxin action with respect to ARF8 inactivation. Although most genes involved in fruit formation remain to be discovered, the general idea is that the outgrowth of the ovary into a fruit is actively inhibited until pollination and fertilisation have occurred.

A number of mutants of tomato have been described which show a certain form of parthenocarpy. The pat mutant has been described as being parthenocarpic although this mutant has pleiotropic effects such as short anthers (homeotic conversions), abnormal stamens and low fertility. Therefore, the pat mutant has not been implemented in commercial breeding for the development of parthenocarpic varieties.

Another potential genetic source for parthenocarpy in tomato is the pat2 mutant. This mutation interacts with growth characteristics of the plant depending on the genetic background which makes this mutation not broadly applicable.

In addition, the pat3/pat4 mutant has been described which is polygenic and which shows a reduced fruit size.

The undesired side effects of the natural mutations have stimulated the research into transgenic approaches to achieve parthenocarpy in tomato. Different transgenic approaches have indeed been described for tomato in which parthenocarpy has been successfully achieved. A number of these approaches interfere with auxin homeostasis or signalling. Overexpression of the auxin biosynthesis gene iaaM under control of an ovule specific promoter such as DefH9 leads to parthenocarpic outgrowth of the fruits. Such approach requires fine-tuning in the sense that optimal levels of auxin production are required for normal fruit outgrowth.

Downregulation of the auxin response factors S1AFR7 or S1ARF8 or the signal transduction factor S1IAA9 leads to parthenocarpy. Furthermore, the downregulation of the so-called AUCSIA genes results in parthenocarpic outgrowth of the fruits. In most cases strong pleiotropic effects are observed such as hollow, malformed fruits or altered leaf morphology.

Transgenic interference with gibberellin signalling can also result in parthenocarpy. For example, downregulation of S1Della gene expression leads to parthenocarpy although also in this case strong pleiotropic effects on fruits and leaves are observed. Other examples of generating parthenocarpy in tomato by transgenesis is through the downregulation of the expression of the chalcone synthase gene or the MADS box genes TM8 and TM29. Also in these examples strong pleiotropic effects are observed.

These examples demonstrate that different approaches which interfere with fruit development can result in a certain form of parthenocarpy, i.e. the initiation of the fruit formation is uncoupled from the triggers generated by the fertilised ovule. In many cases, however, the resulting plant shows pleiotropic effects which seems obvious when interfering with hormone function. There is thus a strong need for a genetic source of parthenocarpy in tomato which allows the formation of fruits independent of fertilisation and which does not lead to strong negative pleiotropic effects.

Citation or identification of any document in this application is not an admission that such document is available as prior art to the present invention.

SUMMARY OF THE INVENTION

It is the object of the present invention to provide tomato mutants that may show fertilisation independent fruit formation. It is a further objective of the present invention to improve the fertilisation independent fruit formation without negative pleiotropic effects on the growth and development of the plant.

The invention thus relates to a tomato plant (*Solanum lycopersicum* L.) which may show fertilisation independent fruit formation, obtainable by crossing a first tomato parent plant with a second tomato parent plant, wherein one of the parents may be a plant grown from seeds of which a representative sample was deposited under one of the NCIMB deposit accession numbers listed in Table 1 or a progeny plant thereof and selecting from the progeny of the cross tomato plants that show fertilisation independent fruit formation. The progeny from which selection is made is suitably F2 progeny.

The tomato plant of the invention essentially does not show pleiotropic effects. The fruits that may be formed independently from fertilisation have one or more of the following characteristics:
(a) a size that is essentially similar to the size of fruits formed after fertilization;
(b) the presence of jelly in the fruit and the at least almost complete absence of seeds;
(c) a coloration and ripening process that is comparable to tomato fruits that are formed after fertilisation.

Seeds of the M4 of six representative mutants were deposited on 19 Jun. 2009 with NCIMB Ltd. (Ferguson Building, Craibstone Estate, Bucksburn, Aberdeen, AB21 9YA). Table 1 shows the deposit accession numbers.

TABLE 1

Deposit accession numbers of parthenocarpic tomato mutants

| Name | Mutant number (internal designation) | NCIMB number |
|---|---|---|
| Solanum lycopersicum | 1667 (M4 1667-09R.452400) | NCIMB 41626 |
| Solanum lycopersicum | 2019 (M4 2019-09R.452500) | NCIMB 41627 |
| Solanum lycopersicum | 3475 (M4 3475-09R.452800) | NCIMB 41628 |
| Solanum lycopersicum | 5364 (M4 5364-09R.453200) | NCIMB 41629 |
| Solanum lycopersicum | 5879 (M4 5879-09R.453500) | NCIMB 41630 |
| Solanum lycopersicum | 6162 (M4 6162-09R.453700) | NCIMB 41631 |

The plants of the invention, showing a fertilization independent fruit formation, in particular without pleiotropic effects, may be made by a mutation method comprising:
(a) treating M0 seeds of a tomato plant species to be modified with a mutagenic agent to obtain M1 seeds;
(b) growing plants from the thus obtained M1 seeds to obtain M1 plants;
(c) optionally repeating step b) and c) n times to obtain M1+n seeds;
(d) germinating the thus obtained M1+n seeds and growing the plants in a greenhouse under practical growing conditions and preventing pollination of the flowers by emasculation; and
(e) selecting plants that show fruit outgrowth from the emasculated flowers.

The mutations may be suitably induced by means of chemical mutagenesis, which may be performed by contacting the seeds with one or more mutagenic agents, in particular alkylating mutagenic agents, such as ethyl methanesulfonate (ems), diethyl sulfate (des), ethyleneimine (ei), propane sultone, N-methyl-N-nitrosourethane (mnu), N-nitros o-N-methylurea (NMU), N-ethyl-N-nitrosourea (enu), sodium azide.

Alternatively, the mutations are induced by means of irradiation, which is for example selected from x-rays, fast neutrons, UV irradiation.

The mutations may also be induced by means of genetic engineering, such as by means of use of chimeric oligonucleotides, homologous recombination, introduction of modified target genes which compete with the endogenous product, downregulation through RNA interference, artificial microRNAs, etc.

According to the invention, the fruits may be characterised by a size similar to the fruits of a fertilised flower, the fruits are normally filled with jelly but the seeds are absent, the fruits show a normal coloration and ripening process.

Seeds of the plants of the invention may be produced by self pollination since the parthenocarpy trait is facultative and only occurs upon emasculation or when the plant is or is made male sterile.

Preferably, the method of the invention may further comprise pyramiding alleles of fertilisation independent fruit formation genes without pleiotropic effects.

The invention further relates to methods for obtaining plants or plant parts with altered genotypes, which plants or plant parts may show fertilisation independent fruit formation without pleiotropic effects.

The plants or plant parts of the invention may have in their genome genetic information which is responsible for the fertilisation independent fruit formation without pleiotropic effects. This genetic information may be present in the deposited seeds and may be introduced into other plants by various means, for example crossing and selecting or by molecular techniques.

Progeny of the plants as claimed may also be part of this invention. Progeny may not be only the first but also all further generations as long as fertilisation independent fruit formation is retained. Progeny typically may have an ancestor that is a plant having the ability to develop fruits independently from fertilisation as is found in plants from seed as deposited. An ancestor is intended to encompass not only the generation immediately prior to the plant but also multiple generations before that. More in particular, the ancestor may be a plant from the deposited seed or a further generation descendent therefrom.

Deposits

The Deposits with NCIMB Ltd. (Ferguson Building, Craibstone Estate, Bucksburn, Aberdeen, AB21 9YA), under deposit accession numbers NCIMB 41626, 41627, 41628, 41629, 41630 and 41631 were made pursuant to the terms of the Budapest Treaty. Upon issuance of a patent, all restrictions upon each deposit will be removed, and each deposit is intended to meet the requirements of 37 CFR §§ 1.801-1.809. Each deposit will be maintained in the depository for a period of 30 years, or 5 years after the last request, or for the enforceable life of the patent, whichever is longer, and will be replaced if necessary during that period.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following detailed description, given by way of example, but not intended to limit the invention solely to the specific embodiments described, may best be understood in conjunction with the accompanying drawings.

FIG. 1 consists of FIGS. 1A-1, 1B-1, 1A-2 and 1B-2 and provides a phenotypic comparison of fruits of parthenocarpic tomato mutant 3475 compared to control fruits. The control fruits are in FIGS. 1A-1 and 1A-2 and are fruits from a tomato plant not having the fertilisation independent fruit formation trait. On the left, pollinated fruits from such a control plant are shown, which fruits contain seeds as can be observed in the cross sections of the fruits of FIG. 1A-2 on the left. On the right side of FIGS. 1A-1 and 1A-2, three fruits resulting from emasculated, non-pollinated flowers of the same control plant not having the fertilization independent fruit formation trait are shown. Fruits resulting from the emasculated, non-pollinated flowers show a very strong reduction in fruit size as compared to the fruits which result from pollinated flowers. In addition, the fruits are hollow and do not contain jelly. FIGS. 1B-1 and 1B-2 show fruits from parthenocarpic mutant 3475. Again, on the left side fruits resulting from pollinated flowers are shown, and on the right side the parthenocarpic fruits resulting from emasculated, non-pollinated flowers. FIGS. 1A-1 and 1B-1 provide a top view of fruits. FIGS. 1A-2 and 1B-2 provide an interior view of fruits. The emasculated mutant at the right of FIG. 1B-2 shows the formation of parthenocarpic seedless fruits that are not hollow and contain jelly. FIG. 1 pertains to Deposit NCIMB 41628.

FIG. 2 consists of FIGS. 2A-1, 2B-1, 2A-2, 2B-2 and 2C. FIG. 3 consists of FIGS. 3A-1, 3B-1, 3A-2, 3B-2 and 3C. FIG. 4 consists of FIGS. 4A-1, 4B-1, 4A-2, 4B-2 and 4C. FIG. 5 consists of FIGS. 5A-1, 5B-1, 5A-2, 5B-2 and 5C FIG. 6 consists of FIGS. 6A-1, 6B-1, 6A-2, 6B-2 and 6C. FIG. 7 consists of FIGS. 7A-1, 7B-1, 7A-2, 7B-2 and 7C. FIG. 8 consists of FIGS. 8A-1, 8B-1, 8A-2, 8B-2 and 8C. FIG. 9 consists of FIGS. 9A-1, 9B-1, 9A-2, 9B-2 and 9C FIG. 10 consists of FIGS. 10A-1, 10B-1, 10A-2, 10B-2 and 10C. FIG. 11 consists of FIGS. 11A-1, 11B-1, 11A-2, 11B-2 and 11C. Each of FIGS. 2A-1, 3A-1, 4A-1, 5A-1, 6A-1, 7A-1, 8A-1, 9A-1, 10A-1, 11A-1, 2A-2, 3A-2, 4A-2, 5A-2, 6A-2, 7A-2, 8A-2, 9A-2, 10A-2, and 11A-2 (i.e., all "A" figures of FIGS. 2-11) show fruits from plants having the fertilisation independent fruit formation trait and wherein the fruits are from flowers that were emasculated. Each of FIGS. 2B-1, 3B-1, 4B-1, 5B-1, 6B-1, 7B-1, 8B-1, 9B-1, 10B-1, 11B-1, 2B-2, 3B-2, 4B-2, 5B-2, 6B-2, 7B-2, 8B-2, 9B-2, 10B-2, and 11B-2 (i.e., all "B" figures of FIGS. 2-11) show fruits from flowers that were NOT emasculated, i.e., fruits from fertilised flowers. Each of FIGS. 2C, 3C, 4C, 5C, 6C, 7C, 8C, 9C, 10C, and 11C tabulate area of the emasculated ("emas.") fruit and the not emasculated ("not emas.") fruit. Each of FIGS. 2A-1, 3A-1, 4A-1, 5A-1, 6A-1, 7A-1, 8A-1, 9A-1, 10A-1, 11A-1, 2B-1, 3B-1, 4B-1, 5B-1, 6B-1, 7B-1, 8B-1, 9B-1, 10B-1, and 11B-1 (i.e., all "-1" figures of FIGS. 2-11) show whole fruit views. Each of FIGS. 2A-2, 3A-2, 4A-2, 5A-2, 6A-2, 7A-2, 8A-2, 9A-2, 10A-2, 11A-2, 2B-2, 3B-2, 4B-2, 5B-2, 6B-2, 7B-2, 8B-2, 9B-2, 10B-2, and 11B-2 (i.e., all "-2" figures of FIGS. 2-11) show interior views of fruit. Thus, FIGS. 2-11 provide a comparison of fruits from plants having the fertilisation independent fruit formation trait and wherein the fruits are from flowers that were emasculated (the "A" figures of FIGS. 2-11) with fruits from flowers that were NOT emasculated (the "B" figures of FIGS. 2-11). FIG. 2 shows a control and provides views from fruits from a plant that does not have the fertilisation independent fruit formation trait (progeny of an M2 plant which was not showing parthenocarpic fruit formation). On the left the fruits from emasculated flowers are strongly reduced in size, are hollow, and do not contain jelly, as compared to the fruits resulting from pollinated flowers of the same plant on the right. The "A" figures of FIGS. 3-11 pertain respectively to fruits from the M3 population of parthenocarpic mutants 1667 (FIG. 3), 2019 (FIG. 4), 3475 (FIG. 5), 5364 (FIG. 7), 5879 (FIG. 9) and 6162 (FIG. 11), and hence pertain respectively to Deposits NCIMB 41626, NCIMB 41627, NCIMB 41628, NCIMB 41629, NCIMB 41630, NCIMB 41631.

DETAILED DESCRIPTION OF THE INVENTION

Figures 1, 1A:
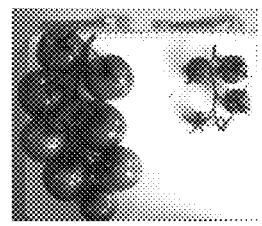

The formation of fruits in tomato is a strongly regulated developmental process involving many genes. A major trigger to initiate fruit development is fertilisation. Fertilisation generates a signal which by its spatial and temporal activity results in outgrowth of the ovary which finally leads to harvestable fruits. It was reasoned that the barrier which is normally lifted through fertilisation associated processes can also be taken away by genetic lesions in genes which have a specific role in restricting the fruit outgrowth before fertilisation has occurred. Most studies so far have interfered with genetic factors involved in hormonal homeostasis and signalling. As plant hormones are involved in a plethora of developmental functions the risk of pleiotropy seems significant.

Most of the genes involved in fruit formation are currently unknown. In the research that led to the present invention it was therefore decided to take an unbiased approach in which random genetic modifications were applied in tomato. Such unbiased approach encompasses a chemical or physical random mutagenesis procedure combined with an efficient phenotypic selection procedure. Such selection procedure is achieved by growing plants under conditions in which the potential for parthenocarpy can be monitored through which those mutants can be identified which have acquired fertilisation independent fruit formation without pleiotropic effects. A clear advantage of such screening approach is that the quality of the trait can be monitored directly, i.e. the vegetative development as well as the normal outgrowth of the seedless fruits in terms of size, shape, jelly formation and ripening can be judged unambiguously.

The approach taken therefore comprises the following steps:
1. Generation of a mutant population by treatment of seeds or plant tissues with mutagenic agents like ethane methylsulfonate (ems).
2. The setup of an efficient phenotypic screen in which selection is based on fruit formation of emasculated flowers which completely prevents pollination and thereby fertilisation. The fruits are seedless and are in terms of their size, shape, jelly formation and ripening comparable to an untreated near isogenic control plant.
3. Characterisation of the selected mutants with respect to parthenocarpy, size, shape, jelly formation and ripening and the absence of pleiotropic effects.

In order to create genetic variability use can be made of induced mutagenesis. Several chemicals or physical treatments are known to the person skilled in the art which can be used to induce genetic mutations in plant species like tomato. For example, one can treat seeds of tomato in a solution containing different concentrations of a mutagen like ems. Ems alkylates primarily G residues of a DNA strand which during DNA replication causes pairing with T instead of C. Therefore, GC basepairs change to AT basepairs at a frequency which is determined by the effective dose of ems and the activity of the mismatch repair system of the plant. The effective dose of ems depends on the concentration used, the seed size and other physical properties and the time of incubation of the seeds in the ems solution.

The seeds which have been treated with ems are typically called M1 seeds. As a consequence of the treatment, the tissues of the M1 seeds contain random point mutations in the genomes of their cells and those present in the subpopulation of cells which will form the germline tissue (germinal cells) will be transferred to the next generation which is called M2. Mutations or combinations thereof which are haplo-insufficient thereby causing sterility or which induce embryo lethality will not be transferred to the M2 generation. A similar procedure as described above for the use of ems applies for other mutagenic agents as well. The M2 population can be used in screening procedures aimed at a reduced triple response of etiolated seedlings. It is obvious to the skilful artisan that any population of tomato plants which carries genetic variation can be taken as starting material for such phenotypic screen.

In order to determine the response of the emasculated flowers of the mutated tomato plants use was made of a normal greenhouse in which 7000 mutated plants were raised and cultivated using practical conditions in terms of nutrition, pruning and pest management. After normal fruit set of the first two trusses had occurred the flowers of the next truss were all emasculated. The outgrowth of fruits of the emasculated flowers was monitored on a regular basis. In those cases in which fruit formation has occurred the fruits are checked for the absence of seeds as well as their size, shape, jelly formation and ripening.

It was surprisingly found that in a low frequency mutants can be identified which show fertilisation independent fruit formation without any pleiotropic effects. Moreover, the fruits are seedless and comparable to the fertilised control fruits with respect to size, shape, jelly formation and ripening. When the parthenocarpic mutants identified in this manner were self-fertilised normal seeded fruits were obtained. Therefore, the parthenocarpic trait identified by this method is facultative.

In order to confirm the genetic nature of the parthenocarpic trait of the identified mutants, the harvested M3 seeds were grown under similar conditions as used for the initial screen. The originally identified parthenocarpic mutants again showed seedless fruits comparable in size, shape, jelly formation and ripening to fertilised control fruits. This confirms the genetic nature of the parthenocapic mutants identified by the approach described by this invention.

Although the parthenocarpic mutants which were identified were comparable, minor differences which were observed may reflect either the presence of different mutant loci or different allelic forms of identical loci affecting this trait in the original population.

In case of recessive mutations these two possibilities can easily be distinguished by carrying out allelism assays which comprise the crossing of the two mutant events which should be or should be made homozygous and determining the phenotype of the hybrid. In case of allelism of the mutations, the parthenocarpic fruit development will be apparent in the F1 whereas in case the phenotype in the mutants is determined by different recessive loci this will not be the case. In case of one event with a dominant mutation and one event with a recessive mutation, the F1 between those two shows the parthenocarpy trait, but when the trait segregates in the F2 it shows that the mutations are not allelic. When the mutations of two events are dominant, then the F1 shows the parthenocarpy trait and the trait segregates in the F2 if they are not allelic, but the whole F2 will express the trait if there is allelism of the mutations.

As random mutagenesis was applied to generate the starting population, mutations in the genetic background may also contribute to the variation of the plant phenotype under the experimental conditions. In order to discriminate between single mutations of different strength and a combined effect of mutation in the genetic background, backcrosses are performed to create uniform genetic backgrounds for the different parthenocarpic events. Such procedure is further relevant in order to determine whether mutations at specific loci involved in parthenocarpy display pleiotropic effects.

In one embodiment the parthenocarpic fruits produced by the plants of the invention are at least 80% seedless as compared to fruits formed after fertilization.

In one embodiment the parthenocarpic fruits produced by the plants of the invention are at least 90% seedless as compared to fruits formed after fertilization.

In one embodiment the parthenocarpic fruits produced by the plants of the invention are at least 95% seedless as compared to fruits formed after fertilization.

In one embodiment the parthenocarpic fruits produced by the plants of the invention are at least 99% seedless as compared to fruits formed after fertilization.

In one embodiment the parthenocarpic fruits produced by the plants of the invention are 100% seedless as compared to fruits formed after fertilization.

In one embodiment, the invention relates to a tomato plant showing the trait fertilization independent or parthenocarpic fruit formation wherein said trait is obtainable by introgression from a plant grown from seed that was deposited with the NCIMB under any one of the accession numbers listed in Table 1.

In one embodiment, the invention relates to a tomato plant, showing the trait fertilization independent or parthenocarpic fruit formation wherein said trait is introgressed from a plant grown from seed that was deposited with the NCIMB under any one of the accession numbers listed in Table 1.

"Introgression" as used herein is intended to mean introduction of a trait into a plant not carrying the trait by means of crossing, backcrossing and selection.

It should be noted that if the selection criterion or criteria is or are clearly defined, the skilled person will be able to identify the descendants that carry the trait in any further generation. For the trait of the invention descendants from a cross between a plant not carrying the parthenocarpic fruit formation trait and a plant carrying the parthenocarpic fruit formation trait as found in plants of which representative seeds were deposited under any one of the accession numbers listed in Table 1 can be identified by growing F2 plants from seeds that are the result from the initial cross and a selfing step, preventing pollination of the plants thus obtained and selecting plants producing fruits as plants showing parthenocarpic fruit formation.

In one embodiment, the invention relates to a tomato plant comprising the fertilization independent fruit formation trait, which plant is obtainable by:
(a) crossing plants, representative seed of which was deposited with the NCIMB under accession number NCIMB 41626, NCIMB 41627, NCIMB 41628, NCIMB 41629, NCIMB 41630 or NCIMB 41631, with a plant not showing the trait to obtain an F1 population;
(b) selfing plants from the F1 population to obtain an F2 population;
(c) preventing pollination of the F2 plants and allowing fruit formation to occur; and
(d) selecting plants producing fruits as plants showing fertilization independent fruit formation.

Pollination can be prevented in various ways. First the flowers can be emasculated.

As an alternative, the plants carrying the parthenocarpy trait that are used in step a) of the above method can be or can be made male sterile, in particular genetically male sterile (GMS) or cytoplasmic male sterile (CMS). Such GMS plants are not plants directly grown from the deposited seeds but carry the parthenocarpy trait as found in plants grown from the deposited seeds. Pollination in step c) of the above method is thus prevented by using tomato plants in step a) that are homozygous for male sterility, and selecting for male sterile plants in the F2 as the means to prevent pollination.

The presence of the genetic information that is responsible for the trait of the invention, i.e. fertilisation independent fruit formation, in the genome of a plant that shows parthenocarpic fruit formation can be determined with the following test. The plant to be tested should be or should be made homozygous for the genetic information responsible for the fertilisation independent fruit formation. The skilled person knows how to obtain a plant that is homozygous for the trait to be tested.

This plant is then crossed with a tester plant that carries the genetic information that is responsible for the trait of the invention in homozygous condition. If the plant to be tested has fertilisation independent fruit formation as a result of the same genetic information that is responsible for the trait of the invention, all progeny plants of the first cross and successive generations will express the trait. If fertilisation independent fruit formation of the plant to be tested is the result of a different part of the genome, e.g. another gene or locus, segregation will occur in either the first cross and/or successive generations. The tester plant can be any plant that carries the genetic information of the invention in homozygous condition, such as plants directly grown from the deposited seeds or progeny thereof that has retained the trait.

In one embodiment of the invention a tomato plant is provided, the fruits of which show fertilisation independent fruit formation and thus when crossed with a tester plant grown from seed as deposited with the NCIMB under any one of the accession numbers as listed in Table 1 which comprises the parthenocarpy trait of the invention, or a progeny plant thereof that comprises the parthenocarpy trait comprised in tomato plants, representative seed of which was deposited with the NCIMB under any one of the accession numbers listed in Table 1 or a plant derived therefrom and comprising the parthenocarpy trait, plants of the first generation progeny (F1) of said cross show a 1:0 segregation for the parthenocarpy trait. In both the tester plant and the plant of the invention the parthenocarpy trait is present in homozygous condition. Plants of the second and further generations, if obtained by selfing, also show a 1:0 segregation for the fertilisation independent fruit formation.

The fertilisation independent fruit formation of the invention has a genetic basis in the genome of the tomato plant. With the above described cross with a tester plant, plants can be identified as being plants of the invention. The tester plant can be any plant of which representative seed was deposited with the NCIMB under accession number NCIMB 41626, NCIMB 41627, NCIMB 41628, NCIMB 41629, NCIMB 41630 or NCIMB 41631. When the genetic information responsible for the parthenocarpy trait as contained in any one of the deposits is present in a plant, the plant is a plant of the invention.

The tomato plants according to the invention may grow inter alia the following fruit types: beef, cherry, cocktail, intermediate, plum, round, etc.

The invention further relates to seed of the tomato plants of the invention and to other parts of the plant that are suitable for sexual reproduction, i.e. propagation material. Such parts are for example selected from the group consisting of microspores, pollen, ovaries, ovules, embryo sacs and egg cells. In addition, the invention relates to parts of the plant that are suitable for vegetative reproduction, in particular cuttings, roots, stems, cells, protoplasts, etc.

According to a further aspect thereof, the invention provides a tissue culture of the tomato plants of the invention. The tissue culture comprises regenerable cells. Such tissue culture can be derived from leaves, pollen, embryos, cotyledon, hypocotyls, meristematic cells, roots, root tips, anthers, flowers, seeds and stems.

The invention also relates to progeny of the tomato plants of the invention. Such progeny can be produced by sexual or vegetative reproduction of a plant of the invention or a progeny plant thereof. The regenerated progeny plant grows fruits independent of fertilisation in the same or a similar way as one of the plants, of which representative seed was deposited (Table 1). This means that such progeny has the same characteristics as claimed for the tomato plants of the invention. In addition to this, the plant may be modified in one or more other characteristics. Such additional modifications are for example effected by mutagenesis or by transformation with a transgene.

As used herein the word "progeny" is intended to mean the offspring or the first and all further descendants from a cross with a plant of the invention that shows fertilization independent fruit formation. Progeny of the invention are descendants of any cross with a plant of the invention that carries the trait that leads to fertilization independent fruit formation.

"Progeny" also encompasses plants that carry the trait of the invention which are obtained from other plants of the invention by vegetative propagation or multiplication.

The invention, furthermore, relates to hybrid seed and to a method of producing hybrid seed comprising crossing a first parent plant with a second parent plant and harvesting the resultant hybrid seed. In case the trait is recessive, both parent plants need to be homozygous for the fertilization independent fruit formation trait in order for the hybrid seed to carry the trait of the invention. They need not necessarily be uniform for other traits.

It is clear that a parent that provides the trait of the invention is not necessarily a plant grown directly from the deposited seeds. The parent can also be a progeny plant from the seed or a progeny plant from seeds that are identified to have or to have acquired the trait of the invention by other means.

In one embodiment, the invention relates to tomato plants that carry the trait of the invention and having acquired said trait by introduction of the genetic information that is responsible for the trait from a suitable source, either by conventional breeding, or genetic modification, in particular by cisgenesis or transgenesis. Cisgenesis is genetic modification of plants with a natural gene, coding for an (agricultural) trait, from the crop plant itself or from a sexually compatible donor plant. Transgenesis is genetic modification of a plant with a gene from a non-crossable species or a synthetic gene.

In one embodiment, the source from which the genetic information is acquired is formed by plants grown from the deposited seeds or sexual or vegetative descendants therefrom.

The invention also relates to the germplasm of plants of the invention. The germplasm is constituted by all inherited characteristics of an organism and according to the invention encompasses at least the fertilization independent fruit formation trait of the invention.

The invention further relates to cells of the tomato plants that show the fertilization independent fruit formation trait. Each cell of such tomato plants carries the genetic information that leads to phenotypic expression of said trait. The cell may be an individual cell or be part of a tomato plant or tomato plant part, such as the tomato fruit.

The invention also relates to the parthenocarpic tomato fruits that are produced by the plants of the invention. In addition, the invention relates to parts of the tomato fruits and processed products produced from the tomato fruits, such as paste, juice, soup, sauce, etc.

In this specification the terms "parthenocarpy", "parthenocarpic fruit formation" and "fertilisation independent fruit formation" are used interchangeably. They all mean that fruits are formed when fertilisation is prevented in some way, in particular by emasculation or because the plant is male sterile, either genetic, cytoplasmic or chemical.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

Genetic Modification of Tomato by Ethyl Methane Sulfonate (EMS)

Seeds of the tomato breeding line TR306 were treated with ems by submergence of approximately 10,000 seeds into an aerated solution of 0.5% (w/v) ems during 24 hours at room temperature.

The treated seeds were germinated and the resulting plants were grown in a greenhouse to produce M2 seeds.

After maturation, M2 seeds were harvested and bulked in one pool. The resulting pool of M2 seeds was used as starting material to identify the individual M2 plants containing fertilisation independent fruit formation.

The efficacy of the genetic modification procedure was assessed by determining the occurrence of bleached plants, which is indicative for chlorophyll loss due to modifications in genes directly or indirectly involved in the formation or accumulation of chlorophyll.

Example 2

Identification of Tomato Plants which have Obtained the Trait of Fertilisation Independent Fruit Formation M2 tomato seeds were germinated in soil and grown to small plantlets. Subsequently, approximately 7000 randomly chosen plants were transferred to a greenhouse in which they were raised according to common tomato cultivation practice. After the first two trusses of each plant have set fruit, all flowers of the third truss were emasculated by hand in order to prevent pollination. The plants were monitored on a regular basis in order to determine which mutants show fertilisation independent fruit formation. The first criterion was the formation of a fruit of a size similar to a normal seeded fruit growing on the same plant as a consequence of pollination and fertilisation. As a second criterion, the fruits were selected which contained no seeds and which were normally filled with jelly. On the basis of these criteria 3 parthenocarpic mutants numbered 3475, 5364 and 5879 were selected as the best events out of the 7000 plants which were monitored in this screen. The fruits of the selected parthenocarpic mutants are shown in FIG. 1.

Example 3

Confirmation of the Fertilisation Independent Fruit Formation in Progeny

Figures 1, 1A, 2:
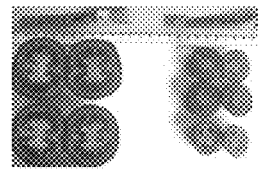
Figures 1, 1B:
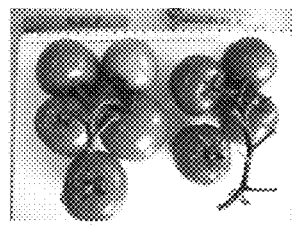
Figures 1, 1B, 2:
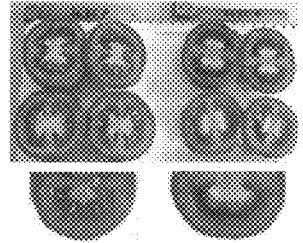

M3 seeds were produced through self pollination of selected parthenocarpic mutants numbered 1667, 2019, 3475, 5364, 5879 and 6162. A total of 7 or 12 plants per M3 population were grown in the greenhouse according to common tomato cultivation practice. As a negative control progeny of M2 plants which were not showing parthenocarpic fruit formation was included in this experiment (FIG. 2). On each plant the flowers of the third truss were emasculated by hand and fruit formation was monitored. It was observed that for each plant of the M3 population derived from mutants 1667 (FIG. 3), 2019 (FIG. 4), 3475 (FIG. 5), 5364 (FIG. 7), 5879 (FIG. 9) and 6162 (FIG. 11) the emasculated truss showed parthenocarpic fruit formation, i.e. the fruits showed a normal size, contained no seeds, were normally filled with jelly and showed a normal ripening. This shows that the parthenocarpic trait identified by the method given by this invention has a genetic basis.

M2 plants of 3475, 5364 and 5879 were also propagated via cuttings. These plants produced fruits that showed the same fruit characteristics as the corresponding M3 plant (FIGS. 6, 8 and 10, respectively).

Example 4

Production of an F1 and F2 Generation

To demonstrate that the fertilisation independent fruit formation trait of the invention can be introduced into other tomato types as well, crosses were made with various other tomato lines. The resulting F1 and/or F2 progeny produced fruits from emasculated flowers that are similar in appearance and characteristics as compared to fruits grown from fertilised flowers of the same plant.

The invention is further described by the following numbered paragraphs:

1. A tomato plant comprising the trait fertilization independent fruit formation wherein said trait is obtainable by introgression from a plant, representative seed of which was deposited with the NCIMB under accession number NCIMB 41626, NCIMB 41627, NCIMB 41628, NCIMB 41629, NCIMB 41630 or NCIMB 41631.

2. A tomato plant comprising the fertilization independent fruit formation trait as paragraphed in paragraph 1, wherein the trait is introgressed from a plant representative seed of which was deposited with the NCIMB under accession number NCIMB 41626, NCIMB 41627, NCIMB 41628, NCIMB 41629, NCIMB 41630 or NCIMB 41631.

3. A tomato plant comprising the fertilization independent fruit formation trait as paragraphed in paragraph 1 or 2, obtainable by:
   a) crossing plants, representative seed of which was deposited with the NCIMB under accession number NCIMB 41626, NCIMB 41627, NCIMB 41628, NCIMB 41629, NCIMB 41630 or NCIMB 41631, with a plant not showing the trait to obtain an F1 population;
   b) selfing plants from the F1 population to obtain an F2 population;
   c) preventing pollination of the F2 plants and allowing fruit formation to occur; and
   d) selecting plants producing fruits as plants showing fertilization independent fruit formation.

4. A tomato plant as paragraphed in paragraph 3, wherein pollination is prevented by emasculating the flowers.

5. A tomato plant as paragraphed in any one of the paragraphs 1-4, wherein the fruit that is formed does essentially not show negative pleiotropic effects.

6. Tomato plant as paragraphed in paragraph 5, wherein the negative pleiotropic effects are selected from hollow fruits, malformed fruits and altered leaf morphology.

7. Tomato plant as paragraphed in any one of the paragraphs 1-6, wherein the fruits that are formed independently from fertilisation have one or more of the following characteristics:
   a) a size that is essentially similar to the size of fruits formed after fertilization;
   b) the presence of jelly in the fruit and the at least almost complete absence of seeds;
   c) a coloration and ripening process that is comparable to tomato fruits that are formed after fertilisation.

8. A tomato plant as paragraphed in any one of the paragraphs 1-7, wherein the tomato plant is a hybrid, doubled haploid, or inbred.

9. A tomato fruit of a plant as paragraphed in any one of the paragraphs 1-8.

10. Tomato fruit as paragraphed in paragraph 9, wherein the fruit is at least 90% seedless, preferably at least 95% seedless, more preferably at least 98% seedless, even more preferably at least 99% seedless, most preferably 100% seedless.

11. Tomato fruit as paragraphed in paragraph 9, wherein the fruit has one or more of the following characteristics:
   a) a size that is essentially similar to the size of fruits formed after fertilization;
   b) the presence of jelly in the fruit and the at least almost complete absence of seeds;
   c) a coloration and ripening process that is comparable to tomato fruits that are formed after fertilisation.

12. Propagation material suitable for producing a plant as paragraphed in any one of the paragraphs 1-8, wherein the propagation material is selected from seeds, parts of the plant that are suitable for sexual reproduction, in particular microspores, pollen, ovaries, ovules, embryo sacs and egg cells, parts of the plant that are suitable for vegetative reproduction, in particular cuttings, roots, stems, cells and protoplasts, tissue cultures of regenerable cells, parts of the plant that are suitable for preparing tissue cultures, in particular leaves, pollen, embryos, cotyledons, hypocotyls, meristematic cells, roots, root tips, anthers, flowers, seeds and stems, wherein the plant produced from the propagation material comprises the fertilisation independent fruit formation trait.

13. Food product, comprising the fruit of a tomato plant as paragraphed in any one of the paragraphs 1-8 or the fruit as paragraphed in any one of paragraphs 9-11, or parts thereof.

14. Food product as paragraphed in paragraph 13, comprising the fruit of a tomato plant as paragraphed in any one of the paragraphs 1-8 or the fruit as paragraphed in any one of paragraphs 9-11 in processed form.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A tomato plant having a fertilisation independent fruit formation trait, wherein the fertilisation independent fruit formed from the plant has jelly, is at least 90% seedless, and is a size that is essentially similar as compared to fruit formed from the same plant after fertilisation; said plant
   having genetic information for expressing the trait, wherein said genetic information includes a mutation, and
   wherein the genetic information responsible for the trait is contained in a plant, representative seed of which was deposited with the NCIMB under accession number NCIMB 41626, NCIMB 41627, NCIMB 41628, NCIMB 41629, NCIMB 41630 or NCIMB 41631.

2. The tomato plant as claimed in claim 1, wherein the trait is introgressed from a parent plant, representative seed of which was deposited with the NCIMB under accession number NCIMB 41626, NCIMB 41627, NCIMB 41628, NCIMB 41629, NCIMB 41630 or NCIMB 41631.

3. The tomato plant as claimed in claim 1, obtained by: a) crossing a plant, representative seed of which was deposited with the NCIMB under accession number NCIMB 41626, NCIMB 41627, NCIMB 41628, NCIMB 41629, NCIMB 41630 or NCIMB 41631, with a plant not showing the fertilisation independent fruit formation trait to obtain an F1 population; b) selfing plants from the F1 population to obtain an F2 population; c) preventing pollination of the F2 plants and allowing fruit formation to occur; and d) selecting plants producing fruit as plants showing fertilisation independent fruit formation.

4. The tomato plant as claimed in claim 3, wherein pollination is prevented by emasculating the flowers.

5. The tomato plant as claimed in claim 1, wherein the tomato plant is a hybrid, doubled haploid, or inbred.

6. A tomato fruit formed independently from fertilisation of the plant as claimed in claim 1.

7. Propagation material for producing the plant as claimed in claim 1, wherein the propagation material is selected from seeds, parts of the plant for sexual reproduction, parts of the plant for vegetative reproduction, and parts of the plant for preparing tissue cultures.

8. A food product comprising the tomato fruit of claim 6, or parts thereof.

9. Tomato fruit as claimed in claim 6, wherein the fruit is at least 95% seedless as compared with fruit of the same plant formed after fertilisation.

10. Tomato fruit as claimed in claim 6, wherein the fruit is at least 98% seedless as compared with fruit of the same plant formed after fertilisation.

11. Tomato fruit as claimed in claim 6, wherein the fruit is at least 99% seedless as compared with fruit of the same plant formed after fertilisation.

12. Tomato fruit as claimed in claim 9, wherein the fruit is 100% seedless as compared with fruit of the same plant formed after fertilisation.

13. Propagation material as claimed in claim 12, wherein the propagation material for sexual reproduction comprises microspores, pollen, ovaries, ovules, embryo sacs or egg cells; the propagation material for vegetative reproduction comprises cuttings, roots, stems, cells or protoplasts; and the propagation material suitable for preparing tissue cultures comprises leaves, pollen, embryos, cotyledons, hypocotyls, meristematic cells, roots, root tips, anthers, flowers, seeds or stems.

14. The tomato plant as claimed in any one of claim 1, 2, 3, 4, or 5; the tomato fruit as claimed in any one of claim 6, 9, 10, 11 or 12; the food product of claim 8; or the propagation material of claim 7 or 13; wherein the representative seed of which was deposited with the NCIMB under accession number NCIMB 41626.

15. The tomato plant as claimed in any one of claim 1, 2, 3, 4, or 5; the tomato fruit as claimed in any one of claim 6, 9, 10, 11 or 13; the food product of claim 8; or the propagation material of claim 7 or 13; wherein the representative seed of which was deposited with the NCIMB under accession number NCIMB 41627.

16. The tomato plant as claimed in any one of claim 1, 2, 3, 4, or 5; the tomato fruit as claimed in any one of claim 6, 9, 10, 11 or 12; the food product of claim 8; or the propagation material of claim 7 or 13; wherein the representative seed of which was deposited with the NCIMB under accession number NCIMB 41628.

17. The tomato plant as claimed in any one of claim 1, 2, 3, 4, or 5; the tomato fruit as claimed in any one of claim 6, 9, 10, 11 or 12; the food product of claim 8; or the propagation material of claim 7 or 13; wherein the representative seed of which was deposited with the NCIMB under accession number NCIMB 41629.

18. The tomato plant as claimed in any one of claim 1, 2, 3, 4, or 5; the tomato fruit as claimed in any one of claim 6, 9, 10, 11 or 12; the food product of claim 8; or the propagation material of claim 7 or 13; wherein the representative seed of which was deposited with the NCIMB under accession number NCIMB 41630.

19. The tomato plant as claimed in any one of claim 1, 2, 3, 4, or 5; the tomato fruit as claimed in any one of claim 6, 9, 10, 11 or 12; the food product of claim 8; or the propagation material of claim 7 or 13; wherein the representative seed of which was deposited with the NCIMB under accession number NCIMB 41631.

\* \* \* \* \*